G. E. MOORE.
ARTIFICIAL LIMB.
APPLICATION FILED MAR. 10, 1921.
Reissued Sept. 13, 1921. 15,192.
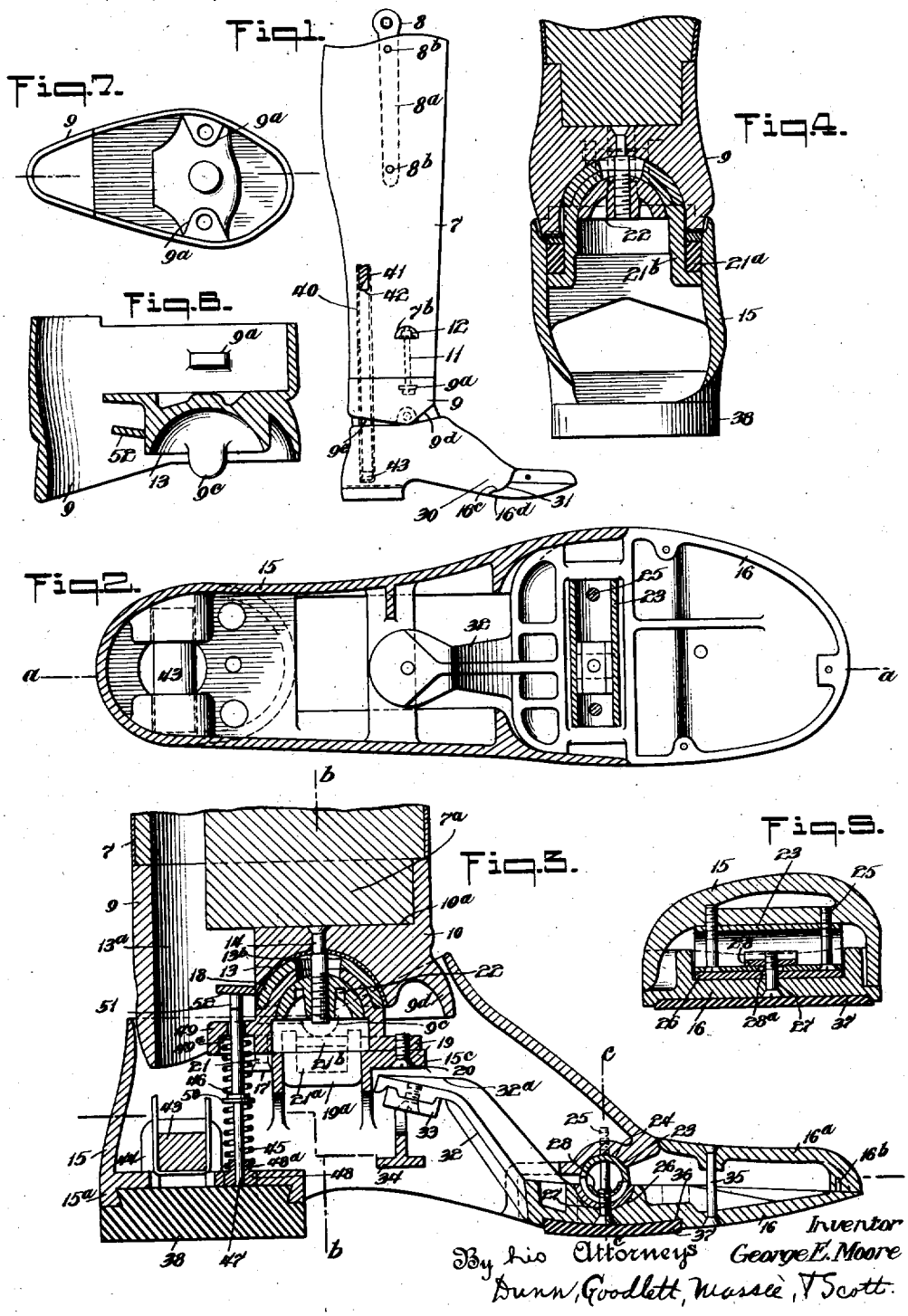

UNITED STATES PATENT OFFICE.

GEORGE E. MOORE, OF PATERSON, NEW JERSEY.

ARTIFICIAL LIMB.

15,192. Specification of Reissued Letters Patent. Reissued Sept. 13, 1921.

Original No. 1,368,348, dated February 15, 1921, Serial No. 316,032, filed August 8, 1919. Application for reissue filed March 10, 1921. Serial No. 451,285.

*To all whom it may concern:*

Be it known that I, GEORGE E. MOORE, a citizen of the United States, residing at Paterson, in the county of Passaic and State of New Jersey, have invented certain new and useful Improvements in Artificial Limbs, of which the following is a full, clear, and concise description.

This invention relates to artificial limbs of the type embodying leg and foot portions connected together for relative movement, and a toe member hinged to the foot member; and has for its object the provision of improved means for controlling and limiting the relative movement of the various portions so as to provide an economical and durable artificial limb which will closely simulate the movements of a natural one.

The invention contemplates the provision of a leg portion having a foot member connected thereto for limited universal movement, a spring suspended stop to limit such movement in one direction and a non-stretchable element to limit such movement in the opposite direction. The invention further contemplates novel means for limiting the relative movement of the toe and foot members which means comprises a rearwardly extending arm carried by the toe member and means contained within the foot for limiting the movement of the arm in either of two directions.

By employing an artificial limb constructed in accordance with this invention, the wearer may maintain his equilibrium when standing, when walking on a level or up or down a grade, and may even climb stairs or ascend a ladder bearing all his weight on the toe member; all with the facility and sureness of a person possessing natural limbs.

One embodiment of the construction which secures these advantages over previously constructed artificial limbs is described in detail hereinafter and is illustrated in the accompanying drawings in which:—

Figure 1 is a side elevation of an artificial leg made in accordance with my invention;

Fig. 2 is a bottom plan view of the foot member;

Fig. 3 is a sectional elevation showing the foot and ankle members and a fragment of the shank portion taken on the line *a—a* of Fig. 2;

Fig. 4 is a transverse section taken on the line *b—b* of Fig. 3;

Fig. 5 is a cross section taken on the line *c—c* of Fig. 3, showing the fore part of the foot member and showing the joint whereby movement of the extremity of said member is permitted;

Fig. 6 is a sectional view of a modified form of an ankle member; and

Fig. 7 is a bottom plan view of the structure shown in Fig. 6.

Referring now to the drawings in detail, in which like characters of reference are employed to designate similar parts throughout the several views, 7 indicates the shank portion of my device which is preferably hollowed out and shaped from a single block of wood to simulate the lines of the human leg. The top of this shank portion is provided with apertured extensions 8, whereby said portion may be attached to an artificial thigh section (not shown) or secured to the stump of the human leg, by means of straps or other suitable appliances (not shown).

In the present embodiment, these extensions comprise an arm $8^a$ which is countersunk in a recess in the exterior of the shank portion and riveted or otherwise secured thereto, as shown at $8^b$, the upper end being of a bifurcated formation to receive a complemental member on the thigh portion of an artificial leg and form a hinge connection therewith in such instances as may be necessary.

When these connecting members 8 are secured in position, the exterior of the shank portion is then preferably covered with rawhide, a thin fabric, or paper, or a like material glued or cemented thereto, which overlies the outer surfaces of the portions $8^a$ of the connecting members and gives the exterior of the shank portion a finish which possesses a skin-like appearance.

The lower end of the shank portion 7 is slightly reduced or inset to fit snugly or telescope within the upper part of the ankle member or section 9, which is preferably a casting of aluminum, or any other suitable or like material, and which possesses a conformation approximating that of the human ankle.

In the formation of casting of this ankle member 9, I provide a wall 10 partially coextensive with the interior dimensions of said member, the upper surface thereof providing a platform $10^a$ on which the base or lower end of the shank portion 7 is adapted to rest or bear, the lower part of said leg portion being of a substantially solid construction to add strength and rigidity thereto, as shown at $7^a$.

To add to the security of the connection between the shank portion 7 and the ankle member 9, the oppositely disposed ears $9^a$ are formed on the interior of the ankle member 9 which carry bolts 11 passing through longitudinal bores in the lower part of the shank portion 7, the lower part of the exterior shank portion which is housed within the upper part of the ankle member 9 being formed with cut-outs, complemental to the said ears. When the shank 7 is seated within the ankle member 9 and rigidly connected thereto by means of the securing nuts 12 on the bolts 11 to which access is afforded through the transverse openings $7^b$ in the shank portion 7, it will be obvious that the shank portion 7 and ankle member 9 will be so joined as to be in effect an integral member.

In the formation of the horizontally disposed wall 10 within the ankle member 9, it is made of a sufficient depth or thickness to permit of the formation of a semi-spherical socket 13 in the under side thereof, faced with a Babbitt metal $13^b$, this socket being apertured at $13^a$ for the reception of a bolt 14, the head of which is countersunk in the upper surface $10^a$ of the wall 10, as shown in Figs. 3 and 4.

The foot member 15, having an integrally formed heel portion $15^a$ and a relatively movable toe portion 16 connected thereto and functioning as hereinafter described, is in the form of a casting of aluminum or any other material which will possess the requisite strength and lightness, and is shaped to approximate the contour of the human member for which it is to form a substitute.

As will be observed, the contour of the upper part and edge of the said foot member 15 is complemental to that of the exterior of the lower portion of the ankle member 9 which fits or telescopes therewithin, as clearly shown in Fig. 3. Extending transversely of the foot member 15, adjacent to the top thereof, is a rib $15^c$ which, in conjunction with the oppositely disposed inwardly directed ears 17 on the interior of said foot member, forms a support for the semi-spherical joint member 18. This latter member is preferably formed on an anti-friction metal supported on a platform 19 to which it may be secured, so as to be substantially integral therewith by welding, brazing, or the like.

The platform 19 has extensions formed to rest upon the rib $15^c$ and the ears 17, and is firmly secured to these members by means of the bolts 20 and 21. Positioned on opposite sides of the platform 19 are U-shaped recesses $19^a$ in which pieces of rubber or a similar resilient material, as indicated at $21^a$, are inserted, this material forming a yielding support for the wood blocks $21^b$ preferably formed of lignum-vitæ or a similar wood which provides bearing surfaces for the downwardly depending ears $9^c$ of the ankle member 9.

From the construction thus far described, it will be obvious that when the inlay $9^d$ of the angle member 9 is positioned within the foot member 15, the ears $9^c$ will rest freely upon the bearing surfaces of the blocks $21^b$ carried by the foot member 15. This will permit of a relative rocking movement of the ankle and foot members on a transverse axis, the extent of the movement of the forepart of the foot member toward the angle member being limited by the non-stretchable cord 40 which is passed around the transversely disposed blocks 41 and 43 carried by the shank and ankle members respectively. The blocks 41 and 43 are preferably of wood, the former being supported in the oppositely located openings 42 in the wall of the shank member, while the latter is frictionally held within the spaced inverted U-shaped ribs 44 in the heel portion of the foot member 15. (See Figs. 1 and 3.)

Assuming that the wearer of my improved artificial leg is performing the movements of walking, it is obvious that as the shank member 7 is thrown forwardly incidental to the completion of the supporting movement of a step and preparatory to taking another step, the cord 40 will become taut and function to raise the heel of the foot member 15 out of contact with the supporting surface.

The movable toe member 16 continues in contact with the supporting surface to the limit of its movement on the hinged joint as hereinafter described, or until the supporting movement of the step is completed. As the limb is raised for the placement of the foot for the next movement of the step, it is apparent that means must be provided for maintaining the sole of the foot in a plane whereby the heel and ball of the foot member 15 will contact with the supporting surface in the same sequence as the corresponding parts of the human member.

This is accomplished by the employment of a yielding floating connection between the ankle and foot members which consists of a pair of expansion springs 45 and 46 mounted on the rod 47. This rod has bearings in the boss 48 located in the heel of the foot member 15 and the lug 49 formed integral with the platform 19 in the ankle member 9, and is provided with an intermediate shoulder 50 forming a bearing surface for the upper end of the spring 45, the lower extremity of which is seated on the shoulder 48[a] of the boss 48. As will be observed, the upper end of the spring 46 is located within the recess 49[a] of the lug 49, while the opposite end thereof rests upon the shoulder 50 of the rod 47.

The tensional resistance of the spring 46 is less than that of the lower spring 45, the two functioning with their coöperating elements to maintain the ankle and foot members in proper relation and control their action with a yielding or cushioning movement. The upward movement of the rod 47 is limited by the plate 52 extending transversely of the angle member 9. This plate is of a harder material than that of the ankle member, steel being preferably used, to form a durable or wear-resisting bearing surface for the case hardened pin 51 set in the upper end of the rod 47. This pin, riding on the under surface of the plate which is inclined upwardly toward the rear of the ankle member, provides for the relative movements of the foot and ankle members without interfering with the functioning of the springs 45 and 46, as aforesaid.

When the ankle member 9 is set or telescoped within the foot member 15, the joint member 18 registers with the complemental socket 13 of the ankle member 9, and the two members 9 and 15 may then be coupled together by threading the convex surfaced nut 22 on the depending end of the bolt 14. This nut 22 is of a size to conform to the interior dimensions of the joint member 18, and, as is evident from the structure shown in Fig. 3, when the ankle and foot members have been united as explained, they will be capable of a relatively universal or rotary movement which will in effect approximate that of the astragalo scaphold joint of the human leg. This is accomplished by the coöperation of the ears 9[c] and their bearings and the components of the ball and socket joint or connection.

As previously pointed out, the toe portion 16 is movable relatively to the remainder of the foot member on a transverse axis, a portion of the forepart of the casting forming the foot member 15 having a semi-annular recess formed therein, as shown at 23, to receive a cylindrical sleeve 24, the said sleeve being immovably held in position within said recess by means of screws 25 or the like. It is manifest of course that in lieu of securing this sleeve in position as described, it may be welded or brazed to the casting, or the sleeve may be formed intetral therewith.

The toe member 16 is formed with a semi-annular recess 26 to provide a bearing surface which is adapted to register and engage with the projecting portion of the surface of the sleeve 24, the said recess 26 being held in movable contact with said sleeve by means of a screw 27 passing through the base of the toe section 16 and seating in a plate 28 curved in cross section, which is positioned within said sleeve 24, said sleeve having a medially located elongated slot 28[a] in the wall thereof through which the shank of said screw is adapted to travel on the movement of said plate. This hinged connection just described, in conjunction with the lugs 30 depending from the opposite sides of the forward extremity of the foot member 15, registering with the complemental recesses 31 on the toe portion 16, provides a strong and substantial articulation between the foot member 15 and the toe member 16, which is spaced forwardly of the vertical plane of the line of cleavage between the foot member 15 and the toe portion 16. When the toe portion 16 moves upwardly in the completion of a step movement by the other foot, as previously described, the underpart 16[d] thereof contiguous to the line of cleavage 16[c] will be thrown relatively downwardly out of alinement with the coöperating part of the foot member, and as soon as the foot is planted forwardly as the support for another step, this under part 16[d] will precede the ball of the foot in making contact with the supporting surface, causing the toe portion 16 to oscillate on the sleeve and assume its normal position. From this it will be seen that the toe portion 16 will be capable of a resistant movement which is substantially similar to that of the forward part of the human foot in performing the movements incidental to walking and the like. The rear part of the toe member 16 is provided with an integrally formed arm 32 perferably of the configuration shown herein, the upper or free extremity of which is provided with a block of rubber or similar material 33 firmly secured thereto, which is adapted to contact with the upper surface of the transverse rib 34 of the foot portion 15, whereby the upward movement of the toe member 16 is limited.

To afford access to the hinged connection between the foot portion 15 and the toe member 16 for the purposes of adjustment and lubrication, I preferably make the upper or top part of the toe member removable, as shown at 16[a], this section being located by means of the registering pins and apertures 16[b], the parts being securely fastened together by the screw 35. (See Fig. 3).

The base of the toe portion is preferably formed with a transverse recess 36 within which a piece 37 of leather, rubber, or a similar material, is inserted and frictionally held to form a yielding tread, the heel 15[a] of the foot member 15 being likewise cut out for the reception of a heel block 38 of any suitable yielding material.

It will be manifest from the foregoing description that an artificial leg constructed in accordance with my invention will not only be capable of movements which will closely follow those of the human leg in the act of walking for instance, but will also have a degree of movement at the ankle joint, whereby the functioning of this joint will accommodate itself to the general bearing of the user. This is a distinct advance in making an artificial leg an efficient article of utility, as, heretofore, by reason of the construction of such devices, the wearer or user was compelled to readjust his bearing to the limited forward and backward movement of the ankle joint. Even then, after an artificial leg of prior constructions had been worn for a considerable time, it was difficult and required considerable effort for the wearer to maintain his balance by reason of this defect. Furthermore, the toe action conforms to the movements of the toe and forepart of the human foot in walking, practically all objectionable stiffness and resultant unsteadiness being eliminated.

My invention not only simulates the movements of the normal human limb, but its construction greatly facilitates the practising of those movements. The method of effecting the connection between the several movable parts, and of reinforcing and supporting one part through the medium of another, provides an artificial leg which possesses great strength and a degree of steadiness which will enable the wearer to maintain an upright position when at rest without any conscious effort.

I claim:

1. An artificial limb having a foot embodying a toe member hinged thereto, a rearwardly extending arm carried by said toe member and means contained within said foot to limit the movement of said arm in either of two directions.

2. An artificial limb having a leg portion and a foot member, connected for relative movement, a toe member hinged to said foot member, an arm extending rearwardly from said toe member, means positioned within said foot member to coöperate with said arm to limit the movement of the toe member relative to said foot member in either of two directions, spring controlled means for limiting the movement of said foot member relative to said leg member in one direction and for moving said foot member relatively to said leg member in the opposite direction and a non-stretchable element for limiting movement in the latter direction.

3. An artificial limb having a leg portion and a foot member connected for relative movement and means for automatically returning the foot member to normal position upon the completion of a step, said means comprising a rod, bearings for said rod carried by said leg and foot members, a shoulder located intermediate the ends of said rod, a pair of springs on said rod, said springs being separated by and abutting against opposite sides of said shoulder, the other ends of said springs abutting against said bearing portions, an incline stop located within said leg portion for limiting the movement of said rod and controlling the movement of said foot relative to said leg portion in one direction and a non-stretchable element connected to said foot member and leg portion respectively to limit the movement of the foot relative to the leg in the opposite direction.

4. An artificial limb comprising in combination an ankle member, a foot member secured thereto, a tubular bearing running transversely of said foot member intermediate the sole and in step portions thereof, a concave cylindrical bushing on said toe member to coöperate with said bearing, means for securing said bushing to said bearing, an extension of said toe member rearward from said bearing and a stop carried by said foot member to coöperate with said extension to limit the movement of said toe member about said bearing.

5. An artificial limb having a leg portion and a foot member, a semi-spherical babbitt-lined socket in the bottom face of said leg portion, a centrally-apertured semi-spherical anti-friction joint member to coöperate with said socket, a platform comprising a centrally-apertured semi-spherical shell portion secured within said foot member to support said joint member, means comprising a bolt passing through said central apertures and a nut coöperating therewith for maintaining said platform, joint member, and socket in coöperative relation; a spring-suspended stop to limit the movement of said foot member relative to said leg portion in one direction, and a non-stretchable element to limit said relative movement in the opposite direction.

6. An artificial limb comprising a foot-member and a toe-member articulated together on a transverse axis, and a stop to limit the upward movement of said toe-member, said toe-member presenting a bearing-surface extending rearward of the vertical plane through said axis, whereby to the limit of said stop said toe-member is swung upwardly and said rearward-extension downwardly with respect to said foot-member by the raising of the heel of said foot-member incident to the advance of the wearer's body in stepping forward upon the other leg, and whereby said toe-member is straightened out by the wearer's planting said rearward-extension on the ground.

GEORGE E. MOORE.